United States Patent [19]
Igaki

[11] Patent Number: 5,817,100
[45] Date of Patent: *Oct. 6, 1998

[54] STENT DEVICE AND STENT SUPPLYING SYSTEM

[75] Inventor: Keiji Igaki, Shiga, Japan

[73] Assignee: Kabushikikaisya Igaki Iryo Sekkei, Shiga, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 532,709

[22] PCT Filed: Feb. 7, 1995

[86] PCT No.: PCT/JP95/00166

§ 371 Date: Dec. 11, 1995

§ 102(e) Date: Dec. 11, 1995

[87] PCT Pub. No.: WO95/20992

PCT Pub. Date: Aug. 10, 1995

[30] Foreign Application Priority Data

Feb. 7, 1994 [JP] Japan .................................. 6-013660

[51] Int. Cl.⁶ .................................................. A61F 11/00
[52] U.S. Cl. ............................. 606/108; 606/194; 623/1; 623/12
[58] Field of Search ..................... 604/108, 195, 604/191; 623/1, 12; 606/108

[56] References Cited

U.S. PATENT DOCUMENTS

| | | | |
|---|---|---|---|
| 4,045,418 | 8/1977 | Sinclair | 260/78.3 |
| 4,922,905 | 5/1990 | Strecker | 606/195 |
| 4,950,227 | 8/1990 | Savin et al. | 604/8 |
| 5,059,211 | 10/1991 | Stack et al. | 606/198 |
| 5,085,629 | 2/1992 | Goldberg et al. | 604/8 |
| 5,100,429 | 3/1992 | Sinofsky et al. | |
| 5,108,416 | 4/1992 | Ryan et al. | |
| 5,116,318 | 5/1992 | Hillstead | 604/96 |
| 5,147,399 | 9/1992 | Dellon et al. | 623/12 |
| 5,158,545 | 10/1992 | Trudell | 604/53 |
| 5,195,984 | 3/1993 | Schatz. | |
| 5,274,074 | 12/1993 | Tang et al. | 528/370 |
| 5,403,341 | 4/1995 | Solar. | |
| 5,409,495 | 4/1995 | Osborn. | |

FOREIGN PATENT DOCUMENTS

| | | | |
|---|---|---|---|
| 2 025 626 | 3/1991 | Canada | A61L 27/00 |
| 0 183 372 A1 | 6/1986 | European Pat. Off. | A61M 29/00 |
| 0282 175 A1 | 9/1988 | European Pat. Off. | A61F 2/06 |
| 0 326 426 A2 | 8/1989 | European Pat. Off. | B29C 61/00 |
| 0364787B1 | 9/1989 | European Pat. Off. | A61F 2/06 |
| 0 420 541 A2 | 9/1990 | European Pat. Off. | A61L 31/00 |
| 0 441 516 A2 | 8/1991 | European Pat. Off. | A61M 29/00 |
| 0 528 039 A1 | 2/1993 | European Pat. Off. | A61L 27/00 |
| 0 553 960 A1 | 4/1993 | European Pat. Off. | A61F 2/06 |
| U-9 014 845 | 2/1991 | Germany | A61M 29/00 |
| 2-174859 | 7/1990 | Japan | A61M 29/00 |
| 3-21262 | 1/1991 | Japan | A61M 29/02 |
| 3-205059 | 9/1991 | Japan | A61L 31/00 |
| 5-103830 | 4/1993 | Japan | A61L 29/00 |
| WO 90/01969 | 3/1990 | WIPO | A61M 29/00 |
| WO 90/04982 | 5/1990 | WIPO | A61L 27/00 |
| WO 91/12779 | 9/1991 | WIPO | A61F 2/04 |
| WO 91/17789 | 11/1991 | WIPO | A61M 29/02 |
| WO 93/06792 | 4/1993 | WIPO | A61F 2/06 |
| WO 93/15787 | 8/1993 | WIPO | A61M 29/00 |

OTHER PUBLICATIONS

Abstract of 63rd Scientific Session, III–72, Supplemental III Circulation, No. 82, No. 4, Oct. 1990.

*Primary Examiner*—Mark Bockelman
*Attorney, Agent, or Firm*—Limbach & Limbach L.L.P.

[57] ABSTRACT

A stent device which can be loaded on any balloon catheter and which permits an arbitrary stent to be employed in combination with an arbitrary catheter. That is, the present invention is directed to a stent device having a stent fitted on the outer peripheral surface of a radially dilatable and contractible tubular cartridge. The stent device is mounted on a balloon-forming portion of a balloon catheter designed for extending the outside diameter of the catheter from a contracted state to a dilated state. The balloon-forming portion is dilated in the vessel for dilating the stent along with the tubular cartridge. The balloon-forming portion and the tubular cartridge are then contracted for detaching the stent from the balloon catheter for supplying the stent within the vessel.

31 Claims, 8 Drawing Sheets

STENT DEVICE AND STENT SUPPLYING SYSTEM

TECHNICAL FIELD

This invention relates to a stent device introduced into a vessel, such as blood vessel, via e.g., a catheter. More particularly, it relates to a stent supplying system employing the stent device.

BACKGROUND ART

Up to now, there is known a vessel stent introduced into the vessel, such as blood vessel, esophagus, trachea, bronchial tubes, bile-duct or ureter for retaining the shape of the vessel. For example, a stent is attached for prohibiting re-constriction of the blood vessel after percutaneous transluminal angioplasty (PTA) on the constricted portion of the blood vessel, such as arterial vessel. The PTA is an operation consisting in introducing a balloon-forming portion attached to the distal end of a catheter in a constricted portion of the blood vessel and dilating the balloon forming portion for dilating the constricted portion for improving the blood flow.

As such stent, a self-expandable stent, which is contracted in diameter under an external pressure and dilated on removing the external pressure, a balloon dilated stent (mechanically expanded stent) dilated by e.g., a balloon and maintained in the dilated state even after removing the balloon, and a shape memory stent formed of a shape memory resin or a shape memory alloy.

There are a variety of sorts of the stent and the catheter or a system constituted by a stent-dilating mechanism, or a so-called stent delivery system.

For example, the stent delivery system employing the balloon dilated stent is classified by the stent holding methods which may be exemplified by a method employing a so-called sleeve (as shown for example in U.S. Pat. No. 4,950,227), a method employing a protective sheath, a method employing an adhesive, and a method of mechanical caulking.

Similarly, the method employing the shape memory stent may be classified into a method exploiting temperature changes for dilation and a method exploiting the phenomenon of maintaining the same shape but of being changed in property, such as strength, with changes in temperature.

Recently, the progress in the field of the catheter is significant. In particular, the balloon catheter is diversified in shaft design, flexibility, material of the ballooning portion and reduction in outside diameter. It is up to the operator to select an optimum type depending upon symptoms or the like in order to achieve good results.

However, with the stent delivery system, such as one employing a balloon dilated stent, the sort of the balloon catheter is defined once the sort of the stent is defined, such that a catheter not desirable has to be used from time to time.

DISCLOSURE OF THE INVENTION

It is an object of the present invention to provide a stent device which can be loaded on any sort of the balloon catheter and which enables an arbitrary stent to be used in combination with an arbitrary catheter.

It is another object of the present invention to provide a stent supply system which enables the stent to be smoothly introduced into the vessel. It is a further object of the present invention to provide a stent device attachment method which enables a stent device to be easily attached to a balloon catheter.

For accomplishing the above objects, the present invention provides a stent device including a stent fitted on the outer peripheral surface of a radially dilatable and contractible tubular cartridge.

With the stent device of the present invention, the sorts of the stent can be selected freely. Thus the stent may be of any desired configuration, such as diamond-meshed, sheet-shaped, knitted, woven or coil-shaped configurations. The stent material may also be optionally selected from metal, synthetic resin and biodegradable materials. Most preferred is a knitted stent formed of fibers of the biodegradable material.

Although the material of the tubular cartridge is optional, such a material as is extendable and contractible radially and hardly extendable and contractible axially is most preferred. The tubular cartridge exhibiting flexibility and ease in bending is preferred in consideration that it is introduced into the vessel.

Although the stent can be simply fitted on the tubular cartridge, it may be held more positively by arranging a sleeve(s) on at least one end and practically on both ends of the tubular cartridge and by overlapping the edge(s) of the sleeve(s) on one or both ends of the stent or by sandwiching both ends of the stent by folded portion(s) on one or both ends of the stent.

Although the stent device can be handled directly, it may be housed within the sheath in the form of a stent housing system for improving the preservation property and for avoiding the chance of the operator's hand directly touching the stent.

This constitutes the second subject-matter of the present application. That is, with the stent housing system according to the second subject-matter of the present application, the stent device is accommodated within a sheath having a weakening line formed along the axis thereof for facilitating splitting along the axis and an operating member for splitting the sheath along the weakening line into split sheath portions.

The stent device is used by being loaded on a balloon catheter and introduced in place in the vessel in this state. This system constitutes the third subject-matter of the present invention. That is, in the stent supplying system according to the third subject-matter of the present invention, the stent device is mounted on a balloon-forming portion of the balloon catheter configured for dilating the catheter from its contracted state to its dilated state. After the stent is radially dilated along with the tubular cartridge by dilating the balloon-forming portion. The balloon-forming portion and the tubular cartridge are contracted for allowing the stent to be detached from the balloon catheter and to be supplied into the inside of the vessel.

With the above-described stent supplying system, a suitable insertion assistant tool may be preferably employed for loading the stent device on the balloon catheter.

The insertion assistant tool, such as a guide wire or a differential-diameter member, is introduced into one end of the tubular cartridge of the stent device, and the stent device is moved along the length of the insertion assistant tool for loading the stent device on the balloon catheter.

In particular, if, in the stent housing system having a guide wire, the guide wire is introduced into the inside of the balloon catheter, and the stent device is moved along the guide wire along with the sheath so as to be loaded on the balloon-forming portion of the balloon catheter, with the sheath being then split along the weakening line into split sheath portions and removed, it is unnecessary for the operator to touch the stent during loading of the stent device on the balloon catheter.

With the stent device of the present invention, since the stent is loaded on the balloon catheter via the tubular cartridge, no limitations are imposed on the types of the stents or the catheters that can be combined together, thus increasing the degree of freedom in selecting the stent and the catheter.

With the stent supplying system employing the above-described stent device, since the stent is dilated with the tubular cartridge, while the tubular cartridge is contracted with contraction of the balloon-forming portion, the dilated stent can be smoothly supplied into the inside of the vessel.

On the other hand, with the method for loading the stent device according to the present invention, since the stent device can be loaded on the balloon catheter via an insertion assistant tool such as a guide wire or a differential-diameter member, a sequence of the stent device loading operations can be carried out smoothly and promptly.

In particular, if the above-described loading operation is carried out with the stent device housed within the splittable sheath, the operator need not touch the stent nor pull out the stent such as with pincers during loading of the stent device on the balloon catheter, so that the stent may be prohibited from becoming deformed.

BEST MODE FOR CARRYING OUT THE INVENTION

Referring to the drawings, illustrative embodiments of the present invention will be explained in detail.

Figure 1:
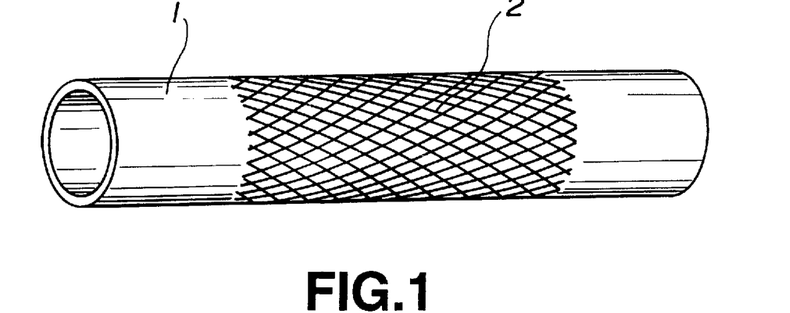
FIG. 1 is a schematic perspective view showing an embodiment of a stent device embodying the present invention.

Referring to FIG. 1, a stent device according to the present invention includes a tubular cartridge 1 of a suitable length and a stent 2 fitted on the outer peripheral surface of the tubular cartridge 1. The stent can be handled in this compact state.

The stent 2 may be of any known construction. For example, a stent formed by knitting biodegradable polymer fiber yarns in a tubular shape may be employed besides a metal stent or cloth stent. The stent formed of biodegradable polymer fibers is highly desirable for a living body since it retains its form for some time after attachment or performs the role of a stent and subsequently disappears by being absorbed by the living tissue.

As the biodegradable polymers, use may be made of polylactic acid (PLA), polyglycolic acid (PGA), polyglactin (polyglycolic acid-polylactic acid copolymer), polydioxanone, polyglycolinate (trimethylene carbonate-glycolid copolymer), or a copolymer of polyglycolic acid or polylactic acid with ε-caprolactone.

On the other hand, the tubular cartridge 1 is preferably expandable and contractible in the radial direction and hardly expandable in the axial direction.

Figure 2A:
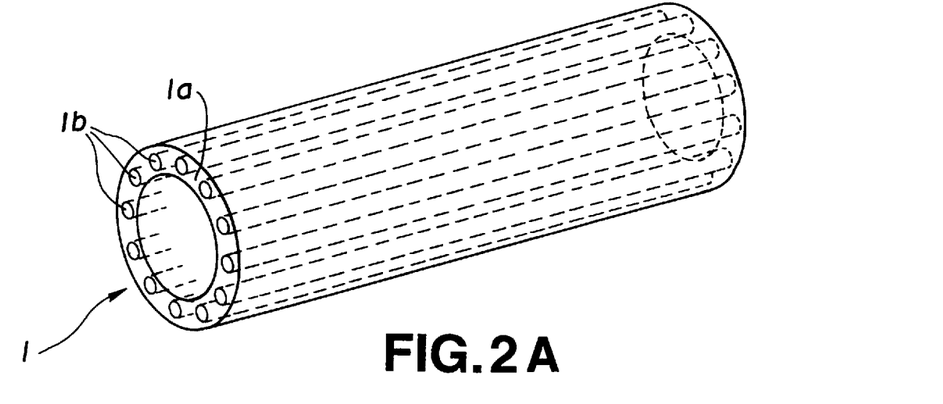
FIG. 2 is a schematic cross-sectional view showing an illustrative construction of a tubular cartridge.

Thus a linear member 1b, formed e.g., of a yarn, exhibiting certain toughness, may be embedded in a extendable tube 1a for extending in the axial direction for constituting the tubular cartridge 1, as shown in FIG. 2A. By this constitution, the axial extension of the tubular cartridge 1 is suppressed by toughness of the linear member 1b.

Figure 2B:
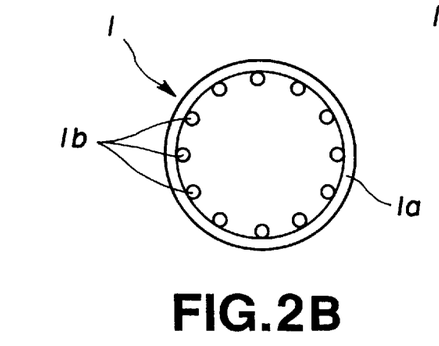
Figure 2C:
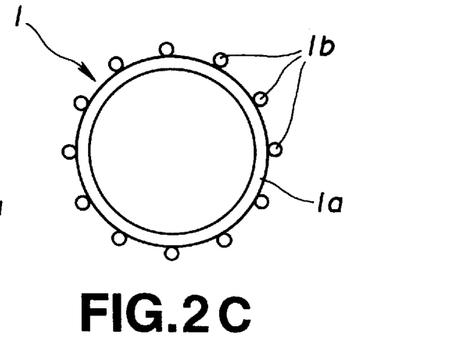

Alternatively, the linear member 1b may be bonded to the inner peripheral surface of the tube 1a, as shown in FIG. 2B, or the linear member 1b may be bonded to the outer peripheral surface of the tube 1a, as shown in FIG. 2C, for realizing similar results.

The axially extendable and contractible portion of the tubular cartridge 1 may comprise an entire or a fractional portion of the tubular cartridge 1.

Figure 3:
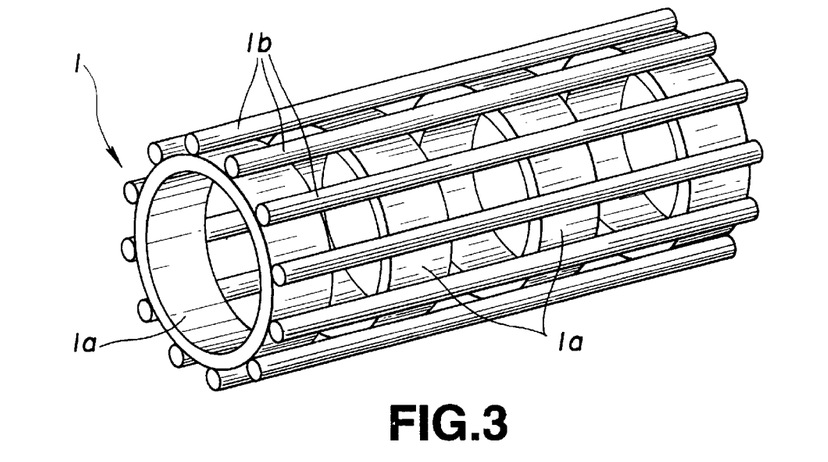
FIG. 3 is a schematic cross-sectional view showing another illustrative construction of a tubular cartridge.

FIG. 3 shows an arrangement in which plural extendable tubes 1a are arranged along the length of the linear member 1b. With this construction, a tubular cartridge may be realized which is hardly extendable along the long axis and which exhibits satisfactory bending and good behavior within the vessel.

In case of such construction, it is preferred that the tube 1a and the linear member 1b be of the similar material in view of adhesion properties. For example, if the tube 1a is of a high polymer material, it is preferred that the linear material 1b be also of a high polymer material.

For securing the tubular cartridge 1 to the stent 2, mechanical caulking, for example, may be employed if the stent 2 is of a metal material. However, not only constraint is placed on the sort of the material of the stent 2, but also the stent 2 tends to be detached before reaching the constricted portion.

Positive securing may be achieved by forming the tubular cartridge 1 of a highly resilient material and by selecting the diameter of the stent 2 to be slightly smaller than the outside diameter of the tubular cartridge 1 for permitting the stent 2 to nip into the peripheral surface of the tubular cartridge 1.

Figure 4:
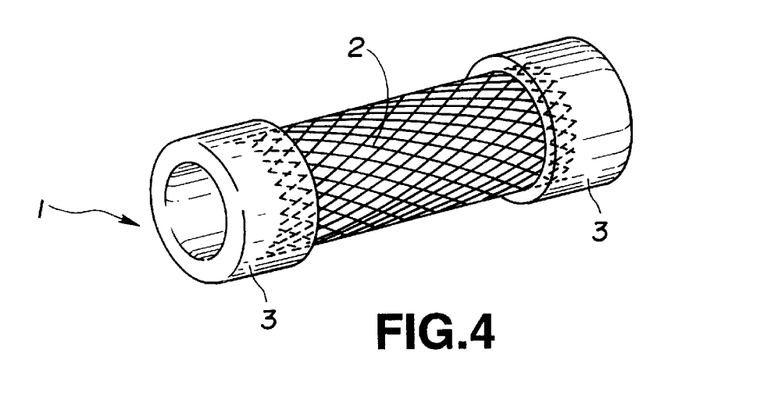
FIG. 4 is a schematic perspective view showing an illustrative construction of a stent holding structure by the tubular cartridge.
Figure 5:
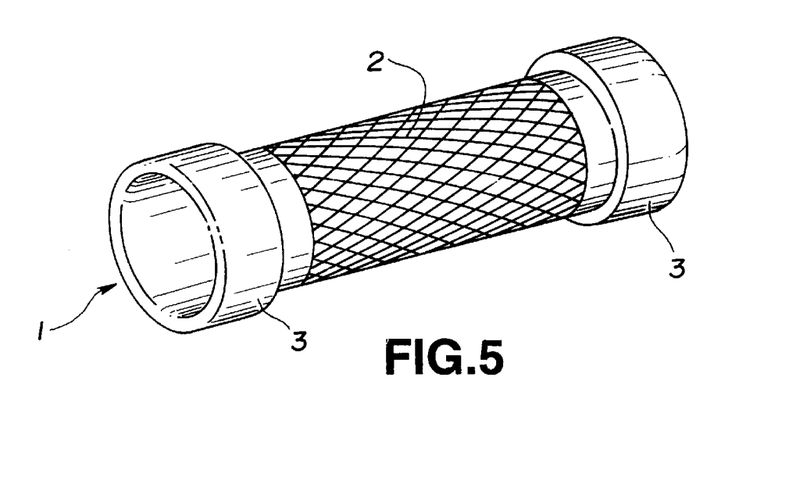
FIG. 5 is a schematic perspective view showing the state in which an end portion of the tubular cartridge is detached from the stent.

Alternatively, both ends of the tubular cartridge 1 may be folded back for sandwiching both ends of the stent 2 for securing the stent 2 by folded-back portions 3. In this case, the diameter t of the tubular cartridge 1 is expanded to T so that the folded-back portions 3 are contracted as shown by arrows so as to be spontaneously detached from both ends of the stent 2, as shown in FIG. 5. By employing a different sort of a material of a main body of the tubular cartridge 1 from the material of the folded-back portion 3, the state of securing the cartridge to the stent may be maintained more reliably.

Figure 8:
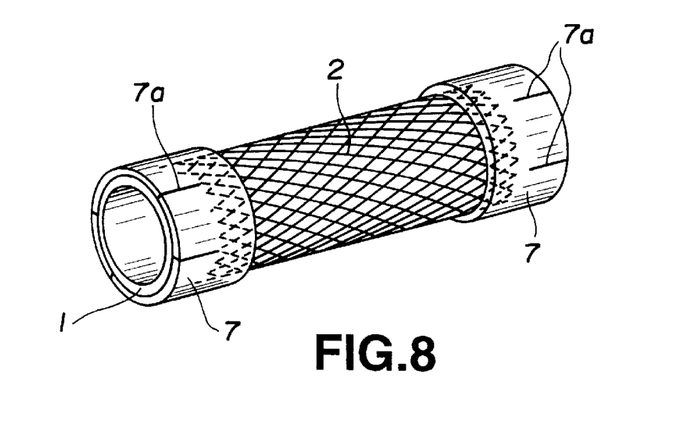
FIG. 8 is a schematic perspective view showing another illustrative stent holding structure by a sleeve.

In place of folding back both ends of the tubular cartridge axial slits 7a, as shown in FIG. 8, the sleeve 7 is torn thereat on dilation of the tubular cartridge 1 for readily detaching the stent 2 from the tubular cartridge 1.

It is possible for a lubricant to be supplied to a space between the sleeve 7a and the stent 2, while it is possible for the lubricant to be coated on the stent 2. This facilitates detachment of the stent 2 from the sleeve 7.

The tubular cartridge 1 or the sleeve 7 may be formed of a radiation impermeable material. This enables the behavior within the vessel to be observed from outside. The radiation impermeable material may be exemplified by a barium salt containing material.

The sleeve 7 may be secured with an adhesive to the tubular cartridge 1. That is, the lubricant may be applied to around the terminal end of the sleeve 7 contacted with the tubular cartridge 1 for preventing the sleeve 7 from becoming axially slipped off the stent 2.

The method of employing the above-mentioned stent device is explained.

Figure 9A:
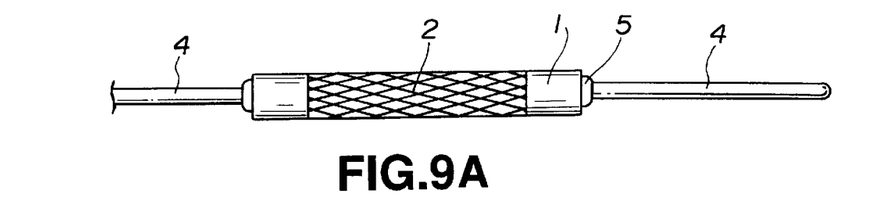
FIG. 9 is a schematic side view for illustrating the method of employing a stent device.

In the present embodiment, the stent 2 is loaded on a balloon-forming portion 5 of a catheter 4 along with the tubular cartridge 1, as shown in FIG. 9A.

Figure 9B:
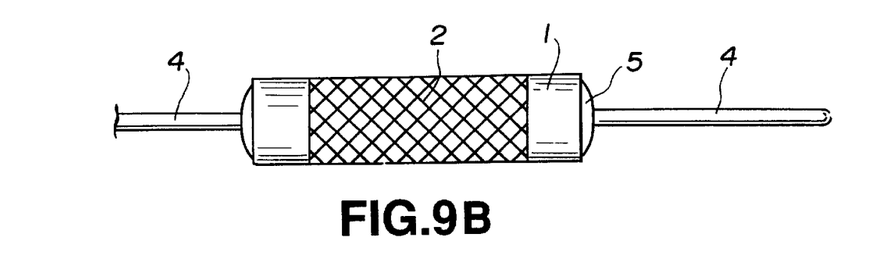

In this state, the stent 2 is shifted to a constricted portion of the vessel. When the stent 2 has reached the constricted portion, the gas or liquid is introduced into the balloon-forming portion 5 for expanding the balloon-forming portion, as shown in FIG. 9B.

With dilation of the balloon-forming portion 5, the tubular cartridge 1 and the stent 2 are also dilated radially.

Figure 9C:
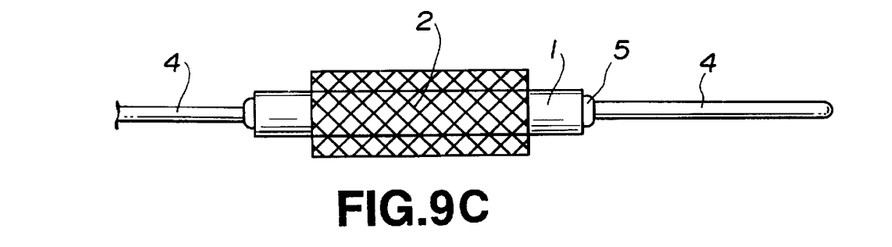

The gas or liquid is then extracted out of the balloon-forming portion 5 for contracting the balloon-forming portion 5, as shown in FIG. 9C. The tubular cartridge 1 is then contracted along with the balloon-forming portion 5, while the stent 2 is maintained in the dilated state.

Figure 9D:
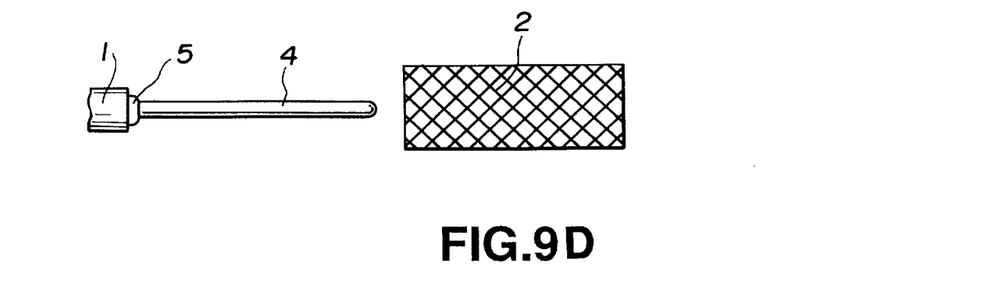
Figure 10A:
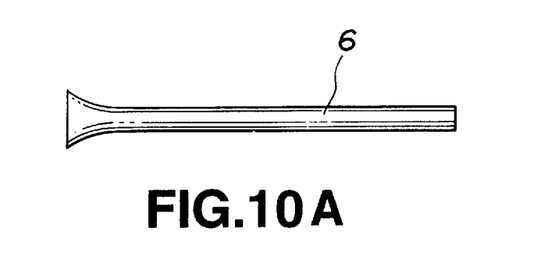
FIG. 10 is a schematic side view showing the method of using various sliders.
Figure 10B:
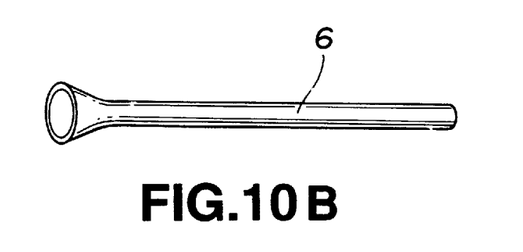
Figure 10C:
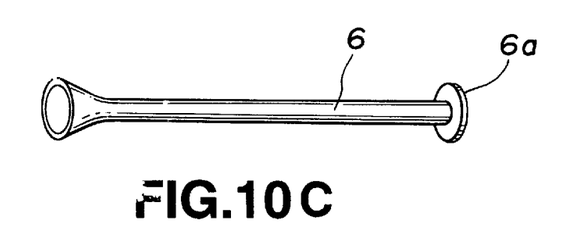
Figure 10D:
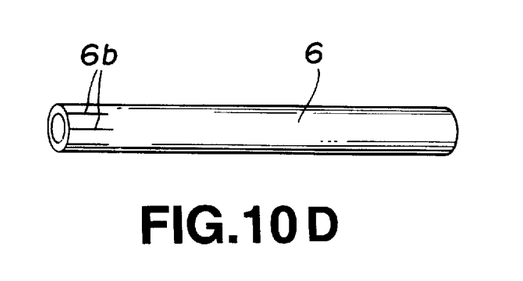

Finally, the catheter 4 is extracted from the constricted portion, as shown in FIG. 9D. Thus the tubular cartridge 1 is extracted along with the balloon-forming portion 5 of the catheter 4 while only the stent 2 is left in the constricted portion.

The stent device of the illustrated embodiment is employed as it is loaded on the balloon catheter, as described above. Thus it is preferred for the stent device to be readily loaded on the balloon catheter during the operation.

Thus it is necessary that an opening of the tubular cartridge 1 be tapered in shape, or the stent device be loaded on the balloon catheter using some sort of an insertion assistant tool.

Such insertion assistant tool may be a guide wire of an extremely thin wire gauge or a differential-diameter member having a progressively increasing diameter. This differential diameter member is referred to hereinafter as a slider. FIG. 10 shows a variety of sorts of sliders 6. Thus, FIGS. 10A, 10B, 10C and 10D show a rod-shaped or so-called solid type slider 6, a hollow type slider 6, a stoppered slider 6 having a stopper 6a and a slider 6 having a scratch 6b, respectively.

Figure 11A:
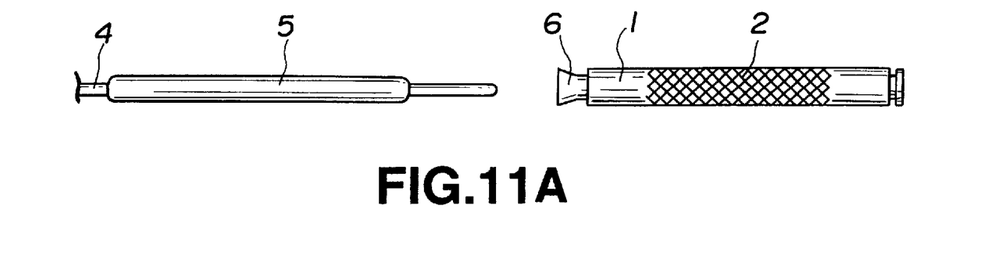
FIG. 11 is a schematic side view for illustrating an operation of attaching the stent device to a balloon catheter.

When loading the stent device, a small-diameter portion of the tubular cartridge 1 is introduced in one end of the tubular cartridge 1, as shown in FIG. 11A.

Figure 11B:
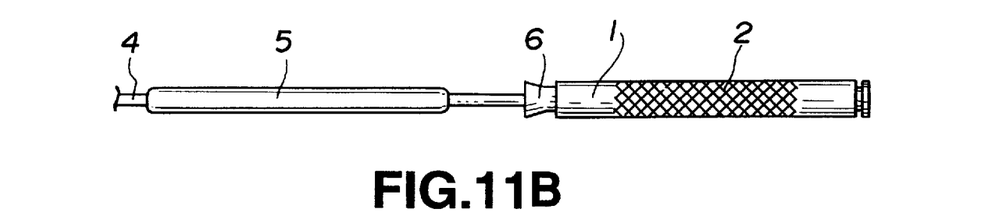
Figure 11C:
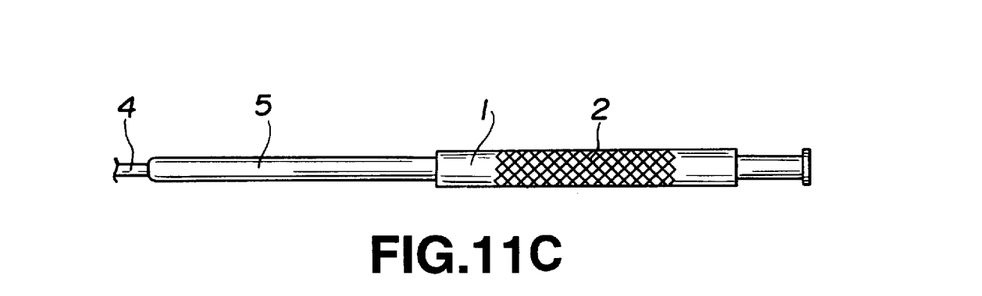

The foremost part of the slider 6 is introduced into a large-diameter end of the slider 6, as shown in FIG. 11B. The tubular cartridge 1 is then moved along with the stent 2 along the length of the slider 6, as shown in FIG. 11C.

Figure 11D:
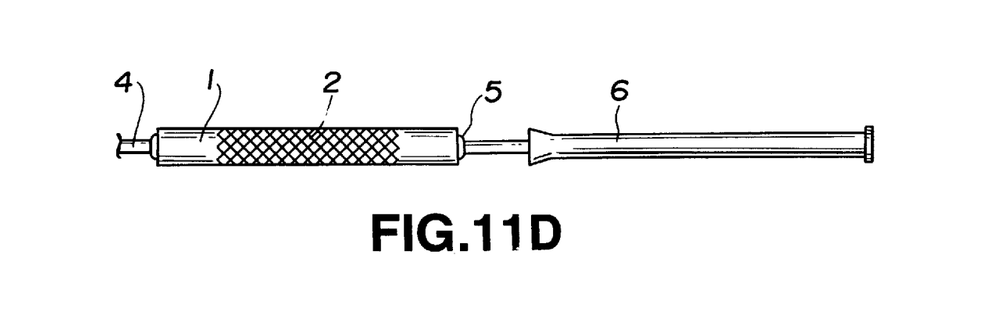
Figure 11E:
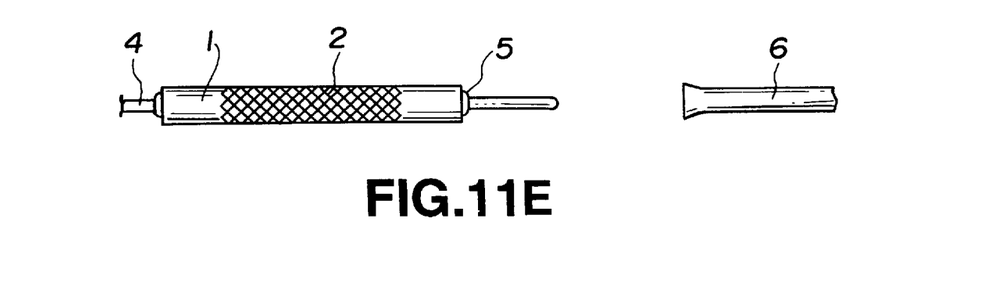

When the tubular cartridge 1 reaches the balloon-forming portion 5, the slider 6 is detached, as shown in FIG. 11D, to complete the loading.

Figure 12:
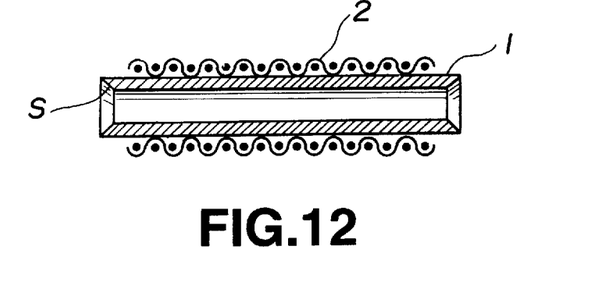
FIG. 12 is a schematic cross-sectional view showing a tapered tubular cartridge.

In place of employing the above-described insertion assistant tool, the inner periphery of at last one end of the tubular cartridge 1 may be tapered at S for facilitating loading of the cartridge on the catheter, as shown in FIG. 12.

While the description has been made of the stent device of the present embodiment and the method of attaching the stent device on the balloon catheter, the stent device of the illustrated embodiment may be enclosed in a splittable sheath for further improving its preservation and handling properties.

Figure 13:
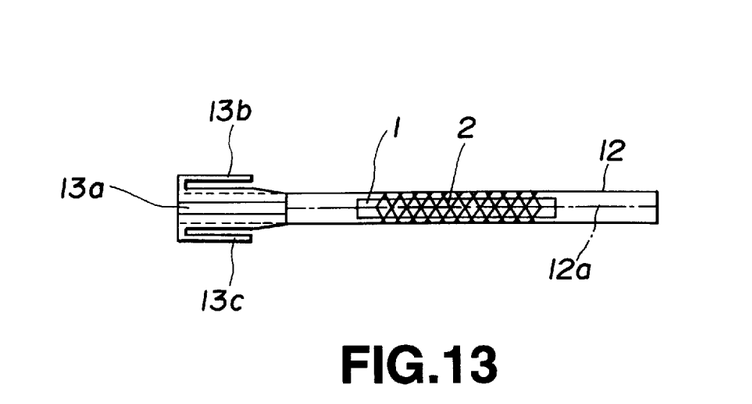
FIG. 13 is a schematic side view showing a stent device having the stent and the tubular cartridge accommodated in a sheath.

That is, as shown in FIG. 13, the tubular cartridge 1 and the stent 2 are accommodated in a sheath 12 fitted with a splitting 1, a holding member produced as a separate element may be attached to each end of the tubular cartridge 1 for securing the stent 2 by this holding member.

The tubular cartridge 1 may be secured to the stent 2 using an adhesive. Since no limitation is put on the sort of the material of the tubular cartridge 1, any arbitrary adhesive may be selectively employed. In contrast, an adhesive needs to be selectively used so as not to damage the balloon in case of direct adhesion to the balloon catheter.

Figure 6:
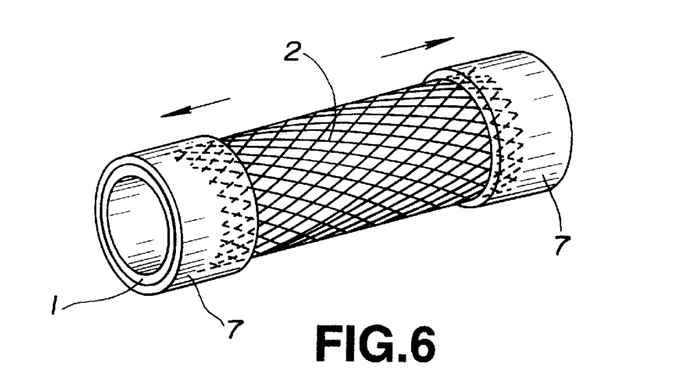
FIG. 6 is a schematic perspective view showing an illustrative stent holding structure by a sleeve.

FIG. 6 shows a an example in which a pair of separately prepared holding members (sleeves) are attached to both ends of the tubular cartridge 1 and these sleeves 7 are used for securing the stent 2.

The sleeve 7 is formed e.g., of silicon resin. Preferably, the sleeve is formed of an elastomer which permits expansion to at least twice the size under an internal pressure available in the balloon catheter while permitting contraction in the axial direction. For example, natural rubber, polyurethane, polyimide, polyether amide, latex or polystyrene, may be employed.

Figure 7:
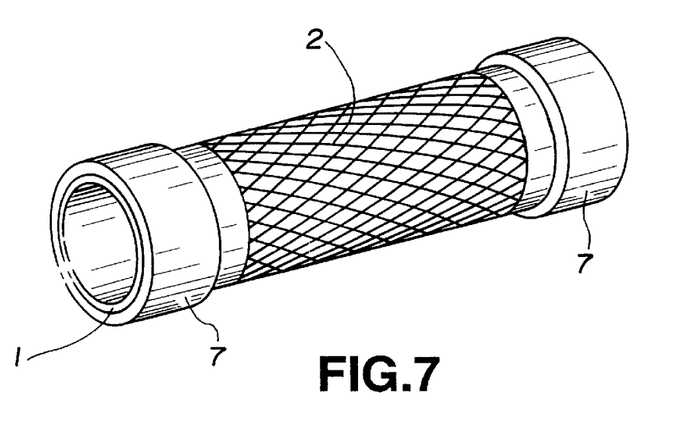
FIG. 7 is a schematic perspective view showing the state in which the sleeve is detached from the stent.

The sleeve is cylindrical in shape and a portion of the sleeve 7 contacted with the stent 2 is designed as an axially extendable flexible portion. Consequently, on dilating the tubular cartridge 1, the sleeve 7 is dilated as shown by arrow so as to be smoothly detached from the stent 2, as shown in FIG. 7. Alternatively, if the sleeve 7 is formed with plural operating member 13.

The sheath 12 is formed of a transparent plastic material, such as polyethylene, and has two axially extending weakening portions 12a, so that it may be split in two along the radial direction. The weakening lines 12a are formed by partially cutting the peripheral surface of the sheath 12 along the wall thickness. Thus the sheath 12 may be easily split along the weakening portions if a moderate force is applied thereat.

Instead of partially cutting in the peripheral wall portion, the sheath 12 may be previously cut in two and these half portions may be then bonded to each other with an adhesive so that the sheath may be divided at the bonded portions. Although the sheath 12 of the illustrated embodiment is formed of a transparent plastic material, it may be semi-transparent or opaque. Alternatively, the stents 2 may be colored differently depending upon the sorts of the stents 2 for facilitating discrimination between different stent sorts.

The sheath 12 has its one end introduced into a splitting operating member 13 having an inner diameter substantially equal to the outer diameter of the sheath 12, and is secured thereto with an adhesive.

The division operating member 13 is similarly formed of a plastic material and has a slightly tapered end of insertion into the sheath 12. The splitting operating member 13 has a slit 13a with a reduced wall thickness in association with the weakening lines 12a of the sheath 12. Thus the division operating member may be easily split in two on application of a certain force, as in the case of the sheath 12.

The splitting operating member 13 is formed with folded operating pieces 13b, 13c in resister with portions of the operating member 13 which are left as a result of the splitting operation. The operating pieces 13b, 13c are in the form of thin sheet pieces folded in the inserting direction of the splitting operating member 13 substantially in the shape of a letter L along the inserting direction of the operating member 13. Thus the operating pieces 13b, 13c may be held by hand or finger so as to be pulled easily.

With the above-described stent device, the tubular cartridge 1 and the stent 2 may be easily taken out by pulling the operating pieces 13c, 13b of the operating member 13.

Figure 14:
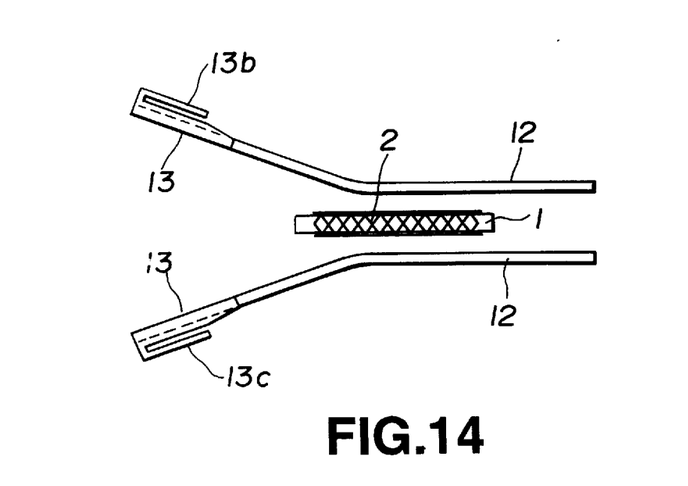
FIG. 14 is a schematic side view showing a torn sheath.

Thus, when the operating pieces 13b, 13c of the splitting operating member 13 are pulled, as shown in FIG. 14, the operating member 13 is torn at the slits 13a, as a result of which the transparent tube 12 is split in two along the weakening lines 12a.

The result is that the tubular cartridge 1 and the stent 2, accommodated within the sheath 12, may be easily taken out without employing pincers etc. This take-out operation may be completed within an extremely short period of time, while the stent is not likely to be deformed. Thus the present embodiment may be employed most advantageously in angioplastic which is in need of prompt operations. In addition, since the sheath 12 may perform the role of a guide when the stent device is introduced into the vessel by the catheter, the stent 2 may be prevented from becoming detached accidentally.

Figure 15:
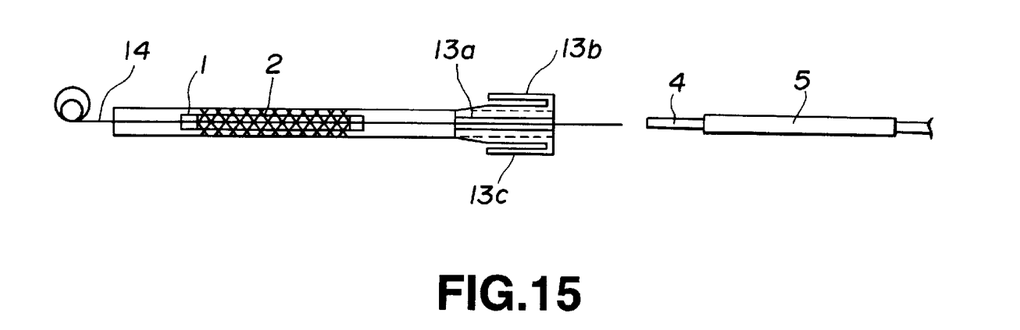
FIG. 15 is a schematic side view showing the method of attaching a stent device accommodated in a sheath to a balloon catheter.
Figure 16:
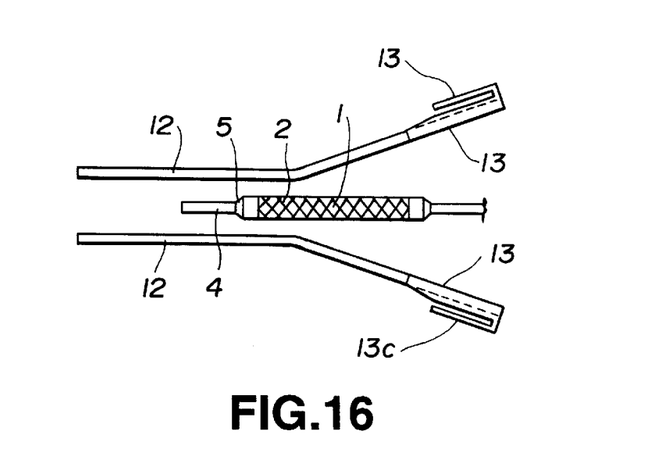
FIG. 16 is a schematic side view showing a sheath torn after attachment thereof on a balloon catheter.

In particular, if, with the use of the stent device having a guide wire 14, the guide wire 14 is introduced into the inside of the balloon catheter 4 and, after shifting the guide wire 14 along the guide wire 14 along with the stent 2, the sheath 12 is split in two and removed, it is unnecessary for the operator to touch the stent 2 manually during loading. The same may be said if the catheter 4 has a guide wire.

For facilitated loading on a catheter, the stent device having the insertion assistant tool as shown in FIG. 10 may be accommodated within the inside of the sheath.

Although description has been made of illustrative embodiments of the present invention, these embodiments are not intended for limiting the invention and various modifications may be made as to the shape or material type without departing from the purport of the invention. For example, anti-thrombotic materials or X-ray impermeable material may be mixed into the material of the tubular cartridge or stent.

It will be seen from the foregoing that, according to the present invention, since the stent is sheathed on a radially extendable tubular cartridge, the operator is free to select the catheter or the stent.

On the other hand, since the stent device of the present invention can be loaded not only on the post-dilation balloon catheter but also on the pre-dilation balloon catheter, balloon catheters can be re-used with significant economic merits.

In addition, with the stent device of the present invention, the stent can be handled in a compact state without imposing unneeded labor on the operator wearing a rubber globe or assistant operators.

Furthermore, if the tubular cartridge and the stent are accommodated within a dividable sheath, not only is preservation property improved, but also the operator is not liable to directly touch the stent during the operation, with the result that there is no risk of the stent becoming deformed and the stent device can be loaded on the catheter in a shorter time for further improving handling property of the stent device.

I claim:

1. A stent device comprising a stent sheathed on a coextensive length of a radially dilatable and contractible freestanding tubular cartridge, wherein said length comprises an elastomeric material having means constructed therewith for permitting radial expansion while opposing lengthening; and wherein said cartridge is radially dilated by a balloon forming catheter for releasing thereby stent.

2. The stent device as claimed in claim 1 characterized in that the tubular cartridge is formed of a radiation impermeable material.

3. The stent device as claimed in claim 2 characterized in that the tubular cartridge contains a barium salt.

4. The stent device as claimed in claim 1 characterized in that a sleeve is fitted on at least one end portion of the tubular cartridge and an edge portion of the sleeve is fitted on an end portion of the stent for holding the stent on said tubular cartridge.

5. The stent device as claimed in claim 4 characterized in that when the stent is radially dilated along with the tubular cartridge, said sleeve is axially contracted so that the edge portion of the stent is detached from the stent.

6. The stent device as claimed in claim 4 characterized in that said sleeve is formed of an elastomer.

7. The stent device as claimed in claim 4 characterized in that said sleeve is formed of a silicon resin.

8. The stent device as claimed in claim 4 further comprising securing means for securing the sleeve at a pre-set position on the tubular cartridge.

9. The stent device as claimed in claim 8 characterized in that said securing means comprises an adhesive.

10. The stent device as claimed in claim 4 characterized in that said sleeve has an axially dilatable and contractible area in which the sleeve is contacted with the stent.

11. The stent device as claimed in claim 4 characterized in that a lubricant is supplied to a space between the sleeve and the tubular cartridge.

12. The stent device as claimed in claim 4 characterized in that the sleeve is formed of a radiation impermeable material.

13. The stent device as claimed in claim 12 characterized in that the sleeve contains a barium salt.

14. The stent device as claimed in claim 1 characterized in that the stent has its both ends held by folded end portions of the tubular cartridge.

15. The stent device as claimed in claim 14 characterized in that, when the stent is radially dilated along with the tubular cartridge, the folded end portions of the tubular cartridge are axially contracted so that the folded end portions release the stent.

16. The stent device as claimed in any one of claims 1 to 15 wherein a lubricant or hydrophilic coating is applied to the stent.

17. The stent device as claimed in any one of claims 1 to 15 characterized in that the stent is formed of a biodegradable polymer.

18. The stent device as claimed in any one of claims 1 to 15 wherein the stent is formed of biodegradable polymer fibers knitted in a tubular shape.

19. A stent insertion system comprising;

a stent sheathed on a coextensive length of a radially dilatable and contractible free-standing tubular cartridge, wherein said length comprises an elastomeric material having means constructed therewith for permitting radial expansion while opposing lengthening; and wherein said cartridge is dilated by a balloon forming catheter for releasing thereby said stent; and an insertion assistant tool for assisting the loading of the tubular cartridge on a balloon forming portion of a balloon catheter.

20. The stent insertion system as claimed in claim 19 characterized in that the insertion assisting tool is a guide wire.

21. The stent insertion system as claimed in claim 19 characterized in that the insertion assisting tool is a differential-diameter member having different diameters at both ends.

22. A stent housing system comprising a sheath and a stent device accommodated therein, said stent device having a stent fitted on a coextensive length of a radially dilatable and contractible freestanding tubular cartridge, wherein said length comprises an elastomeric material having means constructed therewith for permitting radial expansion while opposing lengthening; and wherein said cartridge is dilated by a balloon forming catheter for releasing thereby said stent, said sheath having a weakening line formed along the axis thereof for facilitating splitting along its axis and an operating member for splitting the sheath along said weakening line into split sheath portions.

23. The stent housing system as claimed in claim 22 characterized in that a sleeve is arranged on at least one end of the tubular cartridge and the sleeve has its edge portion fitted on an end of the stent for holding said stent by said tubular cartridge.

24. The stent housing system as claimed in claim 22 characterized in that said stent has both of its ends held by folded portions of both ends of the tubular cartridge.

25. The stent housing system as claimed in any one of claims 22 to 24 characterized in that the stent is formed of biodegradable polymer fibers.

26. The stent housing system as claimed in any one of claims 22 to 24 characterized in that the stent is formed of biodegradable polymer fibers knitted in a tubular shape.

27. The stent housing system as claimed in claim 22 characterized in that a guide wire is introduced into the tubular cartridge of the stent device.

28. A stent supplying system characterized in that a stent device comprising a stent sheathed on a coextensive length of a radially dilatable and contractible freestanding tubular cartridge, wherein said length comprises an elastomeric material having means constructed therwith for permitting radial expansion while opposing lengthening; and wherein said cartridge is dilated by and mounted on a balloon-forming portion of a balloon catheter for releasing said stent, and in that after the stent is radially dilated along with the tubular cartridge by dilating said balloon-forming portion, said balloon-forming portion and said tubular cartridge are radially contracted for allowing the stent to be detached from the balloon catheter.

29. The stent supplying system as claimed in claim 28 characterized in that a sleeve is arranged on at least one end of the tubular cartridge and the sleeve has its edge portion fitted on an end of the stent for holding said stent by said tubular cartridge, and in that, when the stent is radially dilated along with the tubular cartridge, the sleeve is axially contracted so that its edge is detached from the stent.

30. The stent supplying system as claimed in claim 28 characterized in that the stent has its both ends held by folded portions of both ends of the tubular cartridge, and in that, when the stent is radially dilated along with the tubular cartridge, the folded portion of the tubular cartridge are axially contracted so that its edge is detached from the stent.

31. The stent supplying system as claimed in claim 28 characterized in that the stent device is housed in a sheath having a weakening line formed along the axis thereof for facilitating splitting along the sleeve axis and an operating member for splitting the sheath along said weakening line into split sheath portions.

\* \* \* \* \*